United States Patent [19]

Reynolds

[11] Patent Number: 5,981,475

[45] Date of Patent: Nov. 9, 1999

[54] TREATMENT FOR SENSITIVE TEETH

[75] Inventor: Eric Charles Reynolds, Victoria, Australia

[73] Assignees: The University of Melbourne, Parkville; The Victorian Dairy Industry Authority, Abbotsford, both of Australia

[21] Appl. No.: 08/954,985

[22] Filed: Oct. 21, 1997

Related U.S. Application Data

[63] Continuation of application No. 08/362,479, filed as application No. PCT/AU93/00319, Jun. 29, 1993.

[30] Foreign Application Priority Data

Jun. 29, 1992 [AU] Australia .................................. PL3221

[51] Int. Cl.⁶ .................................................. A61K 37/14
[52] U.S. Cl. ..................................... 514/6; 514/7; 514/12; 514/13; 514/21.2
[58] Field of Search .............................. 514/6, 7, 12, 13, 514/21.2

[56] References Cited

U.S. PATENT DOCUMENTS 5,130,123   7/1992   Reynolds et al. ......................... 424/49

FOREIGN PATENT DOCUMENTS

| 2281683 | 5/1984 | Australia . |
| 82/03008 | 9/1982 | WIPO . |
| 87/07615 | 12/1987 | WIPO . |
| 8707615 | 12/1987 | WIPO . |
| 93/03707 | 3/1993 | WIPO . |

OTHER PUBLICATIONS

Derwent Primary Accession No. 92–136696, Class B04, D21, JP,A, 04–077415 (Taiyo Perfumery) Mar. 11, 1987—Abstract.

Patent Abstracts of Japan, JP, A, 01–153621 (Sunstan, Inc.) Jun. 15, 1989.

*Primary Examiner*—Edward J. Cain
*Attorney, Agent, or Firm*—Andrus, Sceales, Starke & Sawall

[57] ABSTRACT

An oral composition for the treatment of dentinal hypersensitivity containing a dentinal hypersensitivity reducing or relieving amount of an active compound selected from casein, a component of casein, a phosphoprotein and a phosphopeptide, or salts thereof containing the amino acyl residues —Ser (P) —Ser (P) —Ser (P) —where Ser (P) is phosphoserine.

13 Claims, No Drawings

TREATMENT FOR SENSITIVE TEETH

This application is a continuation of application Serial No. 08/362,479 filed Feb. 22, 1995 which is a 371 of PCT/AU93/00319 filed Jun. 29, 1993 now abandoned.

FIELD OF THE INVENTION

This invention relates to a method of treating sensitive teeth with an oral composition containing specific phosphoproteins and phosphopeptides, and to oral compositions suitable for that purpose.

BACKGROUND AND RELATED ART

Tooth sensitivity (dentinal hypersensitivity) is a painful response to physical, chemical or thermal stimuli and can affect one in seven dentate adults. Although the clinical features of dentinal hypersensitivity are well described the physiological mechanisms are not as well understood. The most widely accepted theory suggests that dentinal tubules act as channels that enable the different stimuli to reach the pulp and elicit pain. Compounds used in treating hypersensitive dentine include formalin and silver nitrate, glycerine, strontium chloride, dicalcium phosphate, potassium nitrate, sodium fluoride, sodium citrate, calcium hydroxide, resins, potassium oxalate stannous fluoride and cyanoacrylate. It is believed that most of the above agents reduce dentinal hypersensitivity either by mineralizing, or precipitating at, the entrance of the dentinal tubules thereby blocking stimuli.

SUMMARY OF INVENTION

The present invention provides an oral composition for the treatment of dentinal hypersensitivity containing a dentinal hypersensitivity reducing or relieving amount of an active component selected from a casein, a component of casein ($\alpha_s$-casein or $\beta$-casein), a phosphoprotein, and a phosphopeptide or salts thereof which contains a sequence of amino acyl residues —A—B—C—where A, B and C are independently phosphoserine, phosphothreonine, phosphotyrosine, phosphohistidine orphospholysine, inapharmaceutically or physiologically acceptable carrier.

The preferred sequence is —Ser(P)—Ser(P)—Ser(P)— where Ser(P) is phosphoserine. This sequence is found in the phosphoprotein casein and in some casein-derived peptides.

The preferred casein phosphopeptides contain 3 to 40 amino acyl residues and include the sequence —Ser(P)—Ser(P)—Ser(P)—where Ser(P) is phosphoserine.

Tne oral composition may be in the form of a liquid dentifrice, mouthwash, toothpaste, gel, lozenge, tablet, powder or other pharmaceutically acceptable vehicle suitable for use in treating dentinal hypersensitivity.

The preferred oral compositions may also contain an effective amount of phosphatase inhibitor orphosuhopeptide stabilising agent (eg. afluoride, carrageenan, $\beta$-glycerophosphate, vanadate or anionic polymer) (carboxylate polymer eg. Belsperse 161™, vinyl ether maleic acid polymers, sulfonate polymers or phosphonate polymers or polyphosphates or mixtures thereof). The compositions may also contain agents that enhance the desensitising activity of the active component(s) of the composition by stabilising the active component(s) intraorally or by directly enhancing the desensitisation. Such agents include metal ions such as (Fe (Ill). Zn(II) and Al(III), calcium phosphate (CP), calcium fluoride phosphate (CFP).

Tne present invention also provides a method of treating dentinal hypersensitivity comprising contacting the exposec; dentine of a tooth with arn oral composition containing a dentinal hypersensitivity reducing or relieving amount of an active component, selected from a casein, a component of casein ($\alpha_s$-casein or $\beta$-casein), a phosphoprotein, and a phosphopeptide or salts thereof which contains a sequence of amino acyl residues —A—B—C—where A, B and C are independently phosphoserine, phosphothreonine, phosphotyrosine, phosphohistidine or phospholysine, in a pharmaceutically or physiologically acceptable carrier.

DESCRIPTION OF THE PREFFRRED EMBODIMENTS OF INVENTION

Essential in the method for treating dentinal hypersensitivity according to the present invention is the use of casein, its components $\alpha_s$-casein or $\beta$-casein, a phosphoprotein or a phosphopeptide and/or salts thereof. The preferred specific casein phosphopeptides contain from 3 to 40 amino acids including the sequence —Ser(P)—Ser(P)—Ser(P)—where Ser(P) is phosphoserine.

A mixture of casein phosphopeptides (CPP) and/or their salts may be used in the method of the present invention. In this instance it is preferred that those containing the sequence —Ser(P)—Ser(P)—Ser(P)—above predominate. The casein phosphopeptides or mixtures of CPP are preferably substantially pure at least to the extent of not containing unpalatable impurities. The casein phosphopeptides identified as SEQ.ID NO:1, SEQ.ID NO:2, SEQ.ID NO:3, SEQ.ID NO:4, SEQ.ID NO:5, SEQ.ID NO:6, SEQ.ID NO:7, SEQ.ID NO:8, SEQ.ID NO:9 in the "Sequence Listing" below have been found to be particularly useful in the compositions of the present invention.

The preferred casein phosphopeptides can be simply extracted from a casein digest, such digestion maybe chemical or enzymatic with proteolytic enzymes. It is preferred to digest casein with a proteolytic enzyme for example subtilisin (alcalase), pancreatin, trypsin, chymotrypsin, pepsin, papain, thermolysin or pronase Pancreatin or alcalase are the preferred enzymes. The digested casein can then be fractionated into phosphopeptides, containing the sequence —Ser(P)—Ser(P)—Ser(P)—and other phosphorylated and non-phosphorylated peptides. The preferred casein phosphopeptides can be purified using the selective precipitation method described in our International Patent Application PCT/AU92/00175 as a calcium salt. Alternatively, instead of using $CaCl_2$ to aggregate the preferred phosphopeptides other divalent or trivalent metal ions (e.g. $FeCl_3$, $ZnSO_4$, $CaHPO_4$,) can be used to form CPP aggregates [e.g. FeCPP, ZnCPP, calcium phosphate CPP (CPP—CP), calcium fluoride phosphate CPP (CPP—CFP)] which can then be selectively precipitated by ethanol. The sodium salt of the peptides can be formed by ion exchange of the calcium or zinc salts or alternatively by anion exchange chromatography as described in our U.S. Pat. No. 5,015,628. Ultrafiltration tration may be used to separate the CaCPP, FeCPP, ZnCPP, CPP—CP or CPP—CFP complexes from the remainder of the non-active casein peptides as described below.

Casein was prepared by acidifying milk with 0.1 M HCl to pH 4.7 and the precipitate removed by centrifiugation. Casein was converted to the water soluble salt sodium caseinate by neutralizing resuspended casein with NaOH to pH 7.0. A 10% w/v solution of sodium caseinate was prepared and adjusted to pH 8.0. Pancreatin was added to 0.2% w/v and the hydrolysis allowed to proceed to completion at 37° C. with adjustment to pH 8.0 by constant addition of NaOH. The pH of the solution was then adjusted to pH 4.7 with 5 M HCl and the precipitate removed. The supernatant was adjusted to pH 7.0 with NaOH and CaCl$_2$ added to a level of 1.0% w/v. This solution was then diafiltered through an Amicon YM10 membrane with 1.0% CaCl$_2$. The retentate was washed with 1 volume of deionised water. The individual peptides of the CPP preparation were analysed after separation by anion exchange FPLC and reverse phase HPLC as described in our U.S. Pat. No. 5,015,628. Identification of the peptides involved amino acid composition and sequence analyses after conversion of the phosphoseryl residues to S-ethyl cysteinyl residues. A typical CaCPP ultrafiltration preparation from a pancreatic digest of sodium caseinate contains SEQ.ID NO:1, 22.3% w/w; SEQ.ID NO:2, 21.4% w/w; SEQ.ID NO:3, 17.9% wlw; SEQ.ID NO:4, 6.8% w/w; SEQ.ID NO:5, 6.3% w/w; SEQ.ID NO:6, 6.4% w/w; SEQ.ID NO:7, 5.7% w/w; SEQ.ID NO:8, 0.8%; SEQ.ID NO:9, 3.3% w/w and non-active peptides 9.1% w/w. It is important to note that more severe hydrolysis conditions (e.g. high temperatures, extremes of pH and "non-trypsin-like" proteases) will result in deamidated and/or dephosphorylated and/or shorter peptides than detailed in the "Sequence Listing". These shorter and/or deamidated peptides will still have desensitizing activity if they contain the sequence —Ser(P)—Ser(P)—Ser(P)—. It is preferred, however, to control the hydrolysis to minimize breakdown of the CPP and therefore maximize specific activity.

The calcium, ferric or zinc salt of the CPP can be converted to a sodium salt by acidifying a 10% w/v solution of the CPP to a pH around 2.0 and the di and trivalent metal ions removed by diafiltration through a 1,000 molecular mass exclusion limit filter. The retentate is then neutralised to pH 7.0 with NaOH and then diafiltered with water. Alternatively the di- and trivalent metal ions can be removed by ion exchange.

Caseinate or the CPP maybe used as such, or in the form of their alkali metal, alkaline earth metal or transition metal salts. Typical examples are sodium salts, calcium salts, calcium phosphate salts, calcium fluoride phosphate salts, ferric salts, zinc, copper, aluminium, potassium, strontium, magnesium and nickel salts. Sodium, calcium, calcium phosphate, calcium fluoride phosphate, ferric and zinc salts are most preferred. Accordingly it is contemplated that the present invention is not limited to specific salts mentioned herein and that other cationic metal salts of the CPP particularly cationic transition metal salts could be formed and used for the purposes described herein. It is also possible and within the scope of the present invention to have physical combinations of compounds of the prior art (eg. potassium nitrate. SrCl$_2$, potassium oxalate) which are known to desensitize exposed dentine and one or more of casein and/or the CPP. Such compositions may exert a synergistic or additive effect in terms of desensitization.

The method of the present invention involves applying to the teeth a composition comprising casein, casein components or specific CPP. Such a composition usually contains from about 0.01 to about 60% by weight of casein or CPP preferably from about 0.1 to 20% and most preferably 1.0 to 5.0%. Such compositions maybe an aqueous, aqueous-alcohol or alcohol solution or dispersion of casein or the CPP in the form of a mouthwash, dentifrice, toothpaste, toothpowder, gel, lozenge, tablet, chewing gum, or any other suitable form of an oral composition. The pH or these preparations should be between 2 and 10. Preferably the pH should be between 5 and 9.

Desensitizing activity of casein and the CPP can be destroyed by dephosphorylation of the phosphoserines via the action of intra-oral plaque bacterial phosphatase activity. It is desirable, therefore, to stabilize the CPP against phosphatase and peptidase activity. Examples of stabilizing agents to be used in conjunction with the CPP to prevent or inhibit dephosphorylation are fluoride ions, carrageenan, β-glycerophosphate, vanadate, anionic polymers and aggregating divalent and trivalent metal ions [e.g. Fe(III), Ca(II), Zn(II)]. Calcium, ferric and zinc ions aggregate the CPP producing complexes. This aggregate or complex of Fe(III) and CPP is referred to as FeCPP. FeCPP has been shown to be stabilized against intra-oral phosphatase and peptidase activity and also has been shown to have an increased oral retention when compared with NaCPP, and enhanced desensitizing activity. Stabilizing anionic polymers can be selected from the group consisting of a carboxylate polymer. a sulfonate polymer, a polymer having both a sulfonate and a carboxylate moiety, a carboxylate polymer containing phosphonate groups, polymers containing phosphonate groups, polyphosphates and mixtures thereof. An example of stabilizing anionic polymers that are particularly active are the polymeric carboxylates Belsperse 161™ obtained from Ciba-Geigy and vinyl ether maleic acid polymers eg. gantrez.

CPP stabilize calcium phosphate, specifically they bind to spontaneously forming clusters of amorphous calcium phosphate and amorphous calcium fluoride phosphate to produce calcium phosphate CPP and calcium fluoride phosphate CPP complexes or CPP—CP and CPP—CFP respectively. The CPP can bind upto 25 calcium ions, 15 phosphate ions and 5 fluoride ions per molecule. These complexes have been shown to be particularly useful as desensitizing agents as they promote mineralisation of dentine. Using synthetic peptides the active centre of the CPP involved in binding to the dentine has been shown to be the sequence —Ser(P)—Ser(P)—Ser(P)—.

The preferred oral compositions of the present invention are in the form of toothpaste creams or gels, or mouthwashes. Ingredients typically included in toothpastes and gels may be used in toothpaste and gel compositions in accordance with the invention. Suitable ingredients include abrasive polishing materials, sudsing agents, flavoring agents, humectants, binders, sweetening agents, and water. Abrasives which may be used in the compositions of the invention include alumina and hydrates thereof, such as alpha alumina trihydrate, magnesium trisilicate, magnesium carbonate, aluminosilicate, such as calcined aluminium silicate and aluminium silicate, calcium carbonate, zirconium silicate, polymethylmethacrylate, powdered polyethylene, silica xerogels, hydrogels and aerogels and the like. Also suitable as abrasive agents are calcium pryophosphate, insoluble sodium metaphosphate, calcium carbonate, dicalcium orthophosphate, particulate hydroxyapatite and the like. Depending on the form which the oral composition is to take, the abrasive may be present in an amount of from 0 to 70% by weight, preferably 1 to 70% by weight, more preferably from 10 to 70% by weight, particularly for toothpastes.

Humectants contemplated for use in the preferred oral components include glycerol, polyol, sorbitol, polyethylene glycols, propylene glycol, hydrogenated partially hydrolyzed polysaccharides and the like. The humectants are generally present in amounts of from 0 to 80%, preferably 5 to 70% by weight, particularly for toothpastes. Thickeners suitable for use in the invention include silica. Thickeners may be present in toothpaste creams and gels at 0.1 to 20% by weight.

Binders suitable for use in the compositions of the invention include hydroxyethyl cellulose (Natrosol$^R$, and hydroxypropyl cellulose (Kluce$^R$), as well as xanthan gums, Iris moss and gum tragacanth. Binders may be present in the toothpaste of the invention to the extent of from 0.01 to 10%. Sweeteners suitable for use in the present dentifrice, preferably at levels of about 0.1% to 5%, include saccharin.

Fluoride sources used in toothpastes such as sodium fluoride, stannous fluoride, sodium monofluorophosphate, zinc ammonium fluoride, tin ammonium fluoride, calcium fluoride and cobalt ammonium fluoride may be, and preferably are, included for delivering anti-caries benefit. Preferred compositions of the invention include the fluoride source. Fluoride ions are typically provided at a level of from 0 to 1500 ppm, preferably 50 to 1500 ppm, although higher levels up to about 3000 ppm may be used.

Surfactants, such as a soap, anionic, nonionic, cationic, amphoteric and/or zwitterionic, may be present within the range of 0 to 15%, preferably 0.1 to 15%, more preferably 0.25 to 10% by weight. Anionic surfactants are most preferred, such as sodium dodecyl sulfate, sodium lauryl sarcosinate and sodium dodecylbenzene sulfonate. Flavors are usually included in toothpastes in low amounts, such as from 0.01 to about 5% by weight, especially from 0.1 % to 5%.

Ingredients mentioned above as suitable for toothpastes are generally suitable for gels, as will be apparent to one skilled in the art of toothpaste and gel formulation. Thus, except where otherwise noted, references to toothpastes are to be construed as applying to gels as well. Typically, mouthwashes comprise awater/alcohol solution, flavor, humectant, sweetener, sudsing agent, and colorant. The corresponding compounds mentioned above which are used in toothpastes, are generally suitable within the ranges above for mouthwashes as well. Tne mouthwash can include ethanol at a level of from 0 to 60%, preferably from 5 to 30% by weight.

Antibacterial agents. for example phenolics such as Irgasan DP300 (ex Ciba-Geigy) and salicylamides (including salicylanilides), and sources of certain metal ions such as zinc, copper, silver and stannous (e.g. zinc, copper and stannous chloride, and silver nitrate) may also be, and preferably are included. Dyes/colorants suitable for dentifrices, i.e. FD & C Blue #1, FD & C Yellow #10, FD & C Red #40, etc., may be employed in the dentifrices of the invention. Various otiier optional ingredients may be included in the compositions of the invention. such as preservatives, vitamins such as vitamin C and E, other anti-plaque agents such as stannous salts, copper salts, strontium salts and magnesium salts. Also included may be pH adjusting agents, anti-caries agents such as urea. calcium glycerophosphate, sodium trimetaphosphate. anti-staining compounds such as silicone polymers, plant extracts anc mixtures thereof. Additionally, polymers, particularly anionic polymers, such as polycarboxylates or polysulfonates, or polymers containing both a carboxylate and a sulfonate moiety, phosphonate polymers or polyphosphates may be included.

The following Examples further illustrate several preferred embodiments of the invention.

EXAMPLE 1

Typical formulation for a mouthwash, containing caseinate or various CPP salts according to the invention, is as follows:

| | Mouthwash Formulation | | | |
|---|---|---|---|---|
| | % by weight of final composition | | | |
| Ingredients | A | B | C | D |
| Ethanol | 12.5 | 12.5 | 12.5 | 12.5 |
| 70% Sorbitol | 7 | 7 | 7 | 7 |
| Sodium caseinate | — | — | 5 | — |
| NaCPP | — | 5 | — | — |
| ZnCPP | 5 | — | — | — |
| CPP-CFP | — | — | — | 5 |
| Anionic polymer | 0–5 | 0–5 | 0–5 | 0–5 |
| Tween 20 | 0.55 | 0.55 | 0.55 | 0.55 |
| Preservatives* | 0.2 | 0.2 | 0.2 | 0.2 |
| Flavor | 0.1 | 0.1 | 0.1 | 0.1 |
| Dye | <0.01 | <0.01 | <0.01 | <0.01 |
| Sodium Saccharinate | 0.065 | 0.065 | 0.065 | 0.065 |
| Sodium chloride | 0.05 | 0.05 | 0.05 | 0.05 |
| Na acetate | 0.015 | 0.015 | 0.015 | 0.015 |
| Acetic acid | 0.015 | 0.015 | 0.015 | 0.015 |
| $H_2O$ | to 100 | to 100 | to 100 | to 100 |
| pH | 6.5 | 6.5 | 6.5 | 6.5 |

*0.1% methylparaben

The above formulations have been found to exhibit hypersensitivity relieving properties.

EXAMPLE 2

Typical toothpaste formulations, containing caseinate or various CPP salts are as follows:

| | Toothpaste Formulations pH 6–9 | | | |
|---|---|---|---|---|
| | Final Composition (% w/w) | | | |
| | A | B | C | D |
| 70% Sorbitol | 64 | 39 | 64 | 39 |
| Abrasive silica | 10 | 10 | 10 | 10 |
| Thickening silica | 9 | 10 | 9 | 10 |
| NaCPP, ZnCPP or CPP-CFP | — | — | 5 | 5 |
| Polyethylene glycol (PEG 32$^R$) | 5 | 5 | 5 | 5 |
| Sodium caseinate | 5 | 5 | — | — |
| Anionic polymer | 5 | 5 | 5 | 5 |
| Sodium Lauryl Sulfate | 1.5 | 1.5 | 1.5 | 1.5 |
| Flavour | 1 | 1 | 1 | 1 |
| Sodium saccharinate | 0.3 | 0.2 | 0.3 | 0.2 |
| Na Fluoride | 0.24 | 0.24 | 0.24 | 0.24 |
| Preservative (Na Benzoate) | 0.08 | 0.08 | 0.08 | 0.08 |
| Dye | <0.01 | — | <0.01 | — |
| Titanium oxide | — | 1 | — | 1 |
| Xanthan Gum | 0.15 | 0.6 | 0.15 | 0.6 |
| $H_2O$ | to 100 | to 100 | to 100 | to 100 |

The above formulations have been found to exhibit hypersensitivity relieving properties superior to current commercial dental sensitivity toothpastes, such as those containing strontium chloride.

EXAMPLE 3

A formulation for direct application to sensitive teeth containing 30% w/v ZnCPP or 30% NaCPP, 5% CPP—CFP or 5% sodium caseinate in water. This formulation exhibits hypersensitivity relieving properties superior to known professional treatments such as potassium oxaiate.

I claim:

1. An oral composition when used to treat dentinal hypersensitivity, said composition containing a dentinal hypersensitivity reducing or relieving amount of one or more active component(s) selected from a casein, a component of casein ($\alpha_s$-casein or $\beta$-casein), a phosphoprotein, and a phosphopeptide or salts thereof which contains a sequence of amino acyl residues —A—B—C—where A, B and C are independently phosphoserine, phosphothreonine, phosphotyrosine, phosphohistidine or phospholysine, in a pharmaceutically or physiologically acceptable carrier further containing an effective amount of a phosphatase or peptidase inhibitor.

2. The composition of claim 1 wherein said sequence of amino acyl residues is —Ser(P)—Ser(P)—Ser(P)—where Ser(P) is phosphoserine.

3. The composition of claim 1 wherein the material comprises one or more casein phosphopeptides and/or their salts containing from 3 to 40 amino acyl residues including the sequence —Ser(P)—Ser(P)—Ser(P)—where Ser(P) is phosphoserine.

4. The composition of claim 2, wherein the material comprises one or more casein phosphopeptides and/or their salts containing from 3 to 40 amino acyl residues including the sequence —Ser(P)—Ser(P)—Ser(P)—where —Ser(P) is phosphoserine.

5. The composition of claim 3 wherein said casein phosphopeptides are selected from one or more of the casein phosphopeptides identified herein as Seq.Id No: 1 to Seq.Id No: 9.

6. The composition of claim 5 wherein the casein phosphopeptides (CPP) are in the form of divalent or trivalent metal ion complexes.

7. The composition of claim 6 wherein the complexes are selected from CaCPP, FeCPp, ZnCpp, calcium phosphate CPP and calcium fluoride phosphate CPP.

8. The composition of claim 3 wherein said casein phosphopeptides and/or salts thereof are pure at least to the extent of not containing unpalatable impurities.

9. The composition of claim 1 further containing an effective amount of a phosphopeptide stabilizing agent.

10. The composition of claim 9, wherein the inhibitor or stabilizing agent is selected from one or more of a fluoride, carrageenan, $\beta$-glycerophosphate, vanadate, anionic polymers, carboxylate polymers, sulfonate polymers, polymers having both sulfonate and carboxylate moieties, carboxylate polymers containing phosphonate groups, polymers containing phosphonate groups or polyphosphates or mixtures, polymeric carboxylates, vinyl ether maleic acid polymers, and metal ions such as (Fe(|||), Zn(||)and Al(|||).

11. An oral composition when used to treat dentinal hypersensitivity, said composition containing a dentinal hypersensitivity reducing or relieving amount of one or more active component(s) selected from a casein, a component of casein ($\alpha_s$-casein or $\beta$-casein), a phosphoprotein or salts thereof which contain a sequence of amino acyl residues —A—B—C—where A, B and C are independently phosphoserine, phosphothreonine, phosphotyrosine, phosphohistidine or phospholysine, in a pharmaceutically or physiologically acceptable carrier.

12. A method of treating dentinal hypersensitivity, comprising the step of contacting the exposed dentine of a tooth with an oral composition containing a dentinal hypersensitivity reducing or relieving amount of one or more active componentts) selected from a casein, a component of casein ($\alpha_s$-casein or $\beta$-casein), a phosphoprotein, and a phosphopeptide or salts thereof which contains a sequence of amino acyl residues —A—B—C—where A, B and C are independently phosphoserine, phosphothreonine, phosphotyrosine, phosphohistidine or phospholysine, in a pharmaceutically or physiologically acceptable carrier further containing an effective amount of a phosphatase or peptidase inhibitor.

13. A method of treating dentinal hypersensitivity, comprising the step of contacting the exposed dentine of a tooth with an oral composition containing a dentinal hypersensitivity reducing or relieving amount of one or more active component(s) selected from a casein, a component of casein ($\alpha_s$-casein or $\beta$-casein), a phosphoprotein or salts thereof which contain a sequence of amino acyl residues —A—B—C—where A, B and C are independently phosphoserine, phosphothreonine, phosphotyrosine, phosphohistidine or phospholysine, in a pharmaceutically or physiologically acceptable carrier.

* * * * *

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
       (A) LENGTH: 25
       (B) TYPE: Amino Acid
       (D) TOPOLOGY: Linear (ix) FEATURE:
       (A) NAME/KEY: Phosphoserine
       (B) LOCATION: 15
       (D) OTHER INFORMATION: Post-translationally phosphorylated
           serine (ix) FEATURE:
       (A) NAME/KEY: Phosphoserine
       (B) LOCATION: 17
       (D) OTHER INFORMATION: Post-translationally phosphorylated
           serine (ix) FEATURE:
       (A) NAME/KEY: Phosphoserine
       (B) LOCATION: 18
       (D) OTHER INFORMATION: Post-translationally phosphorylated
           serine (ix) FEATURE:
       (A) NAME/KEY: Phosphoserine
       (B) LOCATION: 19
       (D) OTHER INFORMATION: Post-translationally phosphorylated
           serine (xi) SEQUENCE DESCRIPTION: SEQ ID NO: 1:

Arg Glu Leu Glu Glu Leu Asn Val Pro Gly
1               5                   10

Glu Ile Val Glu Ser Leu Ser Ser Ser Glu
            15                  20

Glu Ser Ile Thr Arg
            25

(2) INFORMATION FOR SEQ ID NO: 2:

(i) SEQUENCE CHARACTERISTICS:
       (A) LENGTH: 21
       (B) TYPE: Amino Acid
       (D) TOPOLOGY: Linear (ix) FEATURE:
       (A) NAME/KEY: Pyroglutamate
       (B) LOCATION: 1
       (D) OTHER INFORMATION: A certain amount will exist in this
           form (ix) FEATURE:
       (A) NAME/KEY: Phosphoserine
       (B) LOCATION: 6
       (D) OTHER INFORMATION: Post-translationally phosphorylated
           serine (ix) FEATURE:
       (A) NAME/KEY: Phosphoserine
       (B) LOCATION: 8
       (D) OTHER INFORMATION: Post-translationally phosphorylated
           serine (ix) FEATURE:
       (A) NAME/KEY: Phosphoserine
       (B) LOCATION: 9
       (D) OTHER INFORMATION: Post-translationally phosphorylated

```
              serine (ix) FEATURE:
         (A) NAME/KEY:  Phosphoserine
         (B) LOCATION:  10
         (D) OTHER INFORMATION:  Post-translationally phosphorylated
             serine (ix) FEATURE:
         (A) NAME/KEY:  Phosphoserine
         (B) LOCATION:  17
         (D) OTHER INFORMATION:  Post-translationally phosphorylated
             serine (xi) SEQUENCE DESCRIPTION:  SEQ ID NO:  2:

Gln Met Glu Ala Glu Ser Ile Ser Ser Ser
1               5                   10

Glu Glu Ile Val Pro Asn Ser Val Glu Gln Lys
                15                  20

(2) INFORMATION FOR SEQ ID NO:  3:

(i) SEQUENCE CHARACTERISTICS:
        (A) LENGTH:  24
        (B) TYPE:  Amino Acid
        (D) TOPOLOGY:  Linear (ix) FEATURE:
         (A) NAME/KEY:  Phosphoserine
         (B) LOCATION:  14
         (D) OTHER INFORMATION:  Post-translationally phosphorylated
             serine (ix) FEATURE:
         (A) NAME/KEY:  Phosphoserine
         (B) LOCATION:  16
         (D) OTHER INFORMATION:  Post-translationally phosphorylated
             serine (ix) FEATURE:
         (A) NAME/KEY:  Phosphoserine
         (B) LOCATION:  17
         (D) OTHER INFORMATION:  Post-translationally phosphorylated
             serine (ix) FEATURE:
         (A) NAME/KEY:  Phosphoserine
         (B) LOCATION:  18
         (D) OTHER INFORMATION:  Post-translationally phosphorylated
             serine (xi) SEQUENCE DESCRIPTION:  SEQ ID NO:  3:

Glu Leu Glu Glu Leu Asn Val Pro Gly Glu
1               5                   10

Ile Val Glu Ser Leu Ser Ser Ser Glu Glu
                15                  20

Ser Ile Thr Arg (2) INFORMATION FOR SEQ ID NO:  4:

(i) SEQUENCE CHARACTERISTICS:
        (A) LENGTH:  25
        (B) TYPE:  Amino Acid
        (D) TOPOLOGY:  Linear (ix) FEATURE:
         (A) NAME/KEY:  Phosphoserine
         (B) LOCATION:  11
         (D) OTHER INFORMATION:  Post-translationally phosphorylated
             serine (ix) FEATURE:
         (A) NAME/KEY:  Phosphoserine
```

(B) LOCATION: 12
            (D) OTHER INFORMATION: Post-translationally phosphorylated
                serine (ix) FEATURE:
            (A) NAME/KEY: Phosphoserine
            (B) LOCATION: 13
            (D) OTHER INFORMATION: Post-translationally phosphorylated
                serine (ix) FEATURE:
            (A) NAME/KEY: Phosphoserine
            (B) LOCATION: 16
            (D) OTHER INFORMATION: Post-translationally phosphorylated
                serine (xi) SEQUENCE DESCRIPTION: SEQ ID NO: 4:

Asn Ala Asn Glu Glu Glu Tyr Ser Ile Gly
1               5                   10

Ser Ser Ser Glu Glu Ser Ala Glu Val Ala
                15                  20

Thr Glu Glu Val Lys
                25

(2) INFORMATION FOR SEQ ID NO: 5:

(i) SEQUENCE CHARACTERISTICS:
            (A) LENGTH: 21
            (B) TYPE: Amino Acid
            (D) TOPOLOGY: Linear (ix) FEATURE:
            (A) NAME/KEY: Phosphoserine
            (B) LOCATION: 6
            (D) OTHER INFORMATION: Post-translationally phosphorylated
                serine (ix) FEATURE:
            (A) NAME/KEY: Phosphoserine
            (B) LOCATION: 8
            (D) OTHER INFORMATION: Post-translationally phosphorylated
                serine (ix) FEATURE:
            (A) NAME/KEY: Phosphoserine
            (B) LOCATION: 9
            (D) OTHER INFORMATION: Post-translationally phosphorylated
                serine (ix) FEATURE:
            (A) NAME/KEY: Phosphoserine
            (B) LOCATION: 10
            (D) OTHER INFORMATION: Post-translationally phosphorylated
                serine (ix) FEATURE:
            (A) NAME/KEY: Phosphoserine
            (B) LOCATION: 17
            (D) OTHER INFORMATION: Post-translationally phosphorylated
                serine (xi) SEQUENCE DESCRIPTION: SEQ ID NO: 5:

Gln Met Glu Ala Glu Ser Ile Ser Ser Ser
1               5                   10

Glu Glu Ile Val Pro Asp Ser Val Glu Gln Lys
                15                  20

(2) INFORMATION FOR SEQ ID NO: 6:

(i) SEQUENCE CHARACTERISTICS:
            (A) LENGTH: 21
            (B) TYPE: Amino Acid
            (D) TOPOLOGY: Linear

```
    (ix) FEATURE:
         (A) NAME/KEY:  Phosphoserine
         (B) LOCATION:  6
         (D) OTHER INFORMATION:  Post-translationally phosphorylated
             serine (ix) FEATURE:
         (A) NAME/KEY:  Phosphoserine
         (B) LOCATION:  8
         (D) OTHER INFORMATION:  Post-translationally phosphorylated
             serine (ix) FEATURE:
         (A) NAME/KEY:  Phosphoserine
         (B) LOCATION:  9
         (D) OTHER INFORMATION:  Post-translationally phosphorylated
             serine (ix) FEATURE:
         (A) NAME/KEY:  Phosphoserine
         (B) LOCATION:  10
         (D) OTHER INFORMATION:  Post-translationally phosphorylated
             serine (ix) FEATURE:
         (A) NAME/KEY:  Phosphoserine
         (B) LOCATION:  17
         (D) OTHER INFORMATION:  Post-translationally phosphorylated
             serine (xi) SEQUENCE DESCRIPTION:  SEQ ID NO:  6:

Gln Met Glu Ala Glu Ser Ile Ser Ser Ser
1               5                   10

Glu Glu Ile Val Pro Asp Ser Val Glu Glu Lys
                15                  20

(2) INFORMATION FOR SEQ ID NO:  7:

(i) SEQUENCE CHARACTERISTICS:
         (A) LENGTH:  20
         (B) TYPE:  Amino Acid
         (D) TOPOLOGY:  Linear (ix) FEATURE:
         (A) NAME/KEY:  Phosphoserine
         (B) LOCATION:  7
         (D) OTHER INFORMATION:  Post-translationally phosphorylated
             serine (ix) FEATURE:
         (A) NAME/KEY:  Phosphoserine
         (B) LOCATION:  8
         (D) OTHER INFORMATION:  Post-translationally phosphorylated
             serine (ix) FEATURE:
         (A) NAME/KEY:  Phosphoserine
         (B) LOCATION:  9
         (D) OTHER INFORMATION:  Post-translationally phosphorylated
             serine (ix) FEATURE:
         (A) NAME/KEY:  Phosphoserine
         (B) LOCATION:  15
         (D) OTHER INFORMATION:  Post-translationally phosphorylated
             serine (xi) SEQUENCE DESCRIPTION:  SEQ ID NO:  7:

Asn Thr Met Glu His Val Ser Ser Ser Glu
1               5                   10

Glu Ser Ile Ile Ser Gln Glu Thr Tyr Lys
                15                  20
```

(2) INFORMATION FOR SEQ ID NO: 8:

(i) SEQUENCE CHARACTERISTICS:
        (A) LENGTH: 21
        (B) TYPE: Amino Acid
        (D) TOPOLOGY: Linear (ix) FEATURE:
        (A) NAME/KEY: Phosphoserine
        (B) LOCATION: 8
        (D) OTHER INFORMATION: Post-translationally phosphorylated
            serine (ix) FEATURE:
        (A) NAME/KEY: Phosphoserine
        (B) LOCATION: 9
        (D) OTHER INFORMATION: Post-translationally phosphorylated
            serine (ix) FEATURE:
        (A) NAME/KEY: Phosphoserine
        (B) LOCATION: 10
        (D) OTHER INFORMATION: Post-translationally phosphorylated
            serine (ix) FEATURE:
        (A) NAME/KEY: Phosphoserine
        (B) LOCATION: 16
        (D) OTHER INFORMATION: Post-translationally phosphorylated
            serine (xi) SEQUENCE DESCRIPTION: SEQ ID NO: 8:

```
Lys Asn Thr Met Glu His Val Ser Ser Ser
1               5                   10

Glu Glu Ser Ile Ile Ser Gln Glu Thr Tyr Lys
                15                  20
```

(2) INFORMATION FOR SEQ ID NO: 9:

(i) SEQUENCE CHARACTERISTICS:
        (A) LENGTH: 37
        (B) TYPE: Amino Acid
        (D) TOPOLOGY: Linear (ix) FEATURE:
        (A) NAME/KEY: Phosphoserine
        (B) LOCATION: 4
        (D) OTHER INFORMATION: Post-translationally phosphorylated
            serine (ix) FEATURE:
        (A) NAME/KEY: Phosphoserine
        (B) LOCATION: 6
        (D) OTHER INFORMATION: Post-translationally phosphorylated
            serine (ix) FEATURE:
        (A) NAME/KEY: Phosphoserine
        (B) LOCATION: 22
        (D) OTHER INFORMATION: Post-translationally phosphorylated
            serine (ix) FEATURE:
        (A) NAME/KEY: Phosphoserine
        (B) LOCATION: 24
        (D) OTHER INFORMATION: Post-translationally phosphorylated
            serine (ix) FEATURE:
        (A) NAME/KEY: Phosphoserine
        (B) LOCATION: 25
        (D) OTHER INFORMATION: Post-translationally phosphorylated
            serine (ix) FEATURE:
        (A) NAME/KEY: Phosphoserine
        (B) LOCATION: 26

-continued

```
        (D) OTHER INFORMATION: Post-translationally phosphorylated
            serine (ix) FEATURE:
        (A) NAME/KEY: Phosphoserine
        (B) LOCATION: 33
        (D) OTHER INFORMATION: Post-translationally phosphorylated
            serine (xi) SEQUENCE DESCRIPTION: SEQ ID NO: 9:

Asp Ile Gly Ser Glu Ser Thr Glu Asp Gln
1               5                   10

Ala Met Glu Asp Ile Lys Gln Met Glu Ala
                15                  20

Glu Ser Ile Ser Ser Ser Glu Glu Ile Val
                25                  30

Pro Asn Ser Val Glu Gln Lys
                35
```